(12) United States Patent
Evans

(10) Patent No.: US 10,433,524 B2
(45) Date of Patent: Oct. 8, 2019

(54) THERAPEUTIC TOY DEVICE FOR AN ANIMAL

(71) Applicant: Mary Beth Evans, San Jose, CA (US)

(72) Inventor: Mary Beth Evans, San Jose, CA (US)

(*) Notice: Subject to any disclaimer, the term of this patent is extended or adjusted under 35 U.S.C. 154(b) by 0 days.

(21) Appl. No.: 16/414,519

(22) Filed: May 16, 2019

(65) Prior Publication Data

US 2019/0269100 A1 Sep. 5, 2019

Related U.S. Application Data

(63) Continuation-in-part of application No. 15/390,482, filed on Dec. 24, 2016, now Pat. No. 10,299,464.

(60) Provisional application No. 62/298,648, filed on Feb. 23, 2016.

(51) Int. Cl.
  *A01K 15/02* (2006.01)
  *A61M 21/02* (2006.01)
  *A61M 21/00* (2006.01)

(52) U.S. Cl.
  CPC ........... *A01K 15/026* (2013.01); *A61M 21/02* (2013.01); *A61M 2021/0022* (2013.01); *A61M 2205/59* (2013.01); *A61M 2250/00* (2013.01)

(58) Field of Classification Search
  CPC ....... A01K 15/026; A01K 15/025; A63H 3/36
  USPC ......... 119/709, 707, 702; 446/268, 373, 370
  See application file for complete search history.

(56) References Cited

U.S. PATENT DOCUMENTS

| | | | | |
|---|---|---|---|---|
| 5,195,917 A | * | 3/1993 | Russell | A63H 3/16 428/100 |
| 5,480,341 A | * | 1/1996 | Plakos | A63H 3/16 434/274 |
| 5,870,971 A | * | 2/1999 | Krietzman | A01K 15/025 119/707 |
| 6,112,703 A | * | 9/2000 | Handelsman | A01K 15/026 119/707 |
| 6,929,527 B1 | * | 8/2005 | Chan | A63H 3/46 446/369 |
| 8,025,550 B2 | * | 9/2011 | Tsengas | A01K 15/025 119/707 |
| 8,312,844 B2 | * | 11/2012 | Mann | A01K 15/025 119/709 |
| 9,282,724 B2 | * | 3/2016 | Nunn | A01K 15/025 |
| 2002/0002022 A1 | * | 1/2002 | Wilcox | A63H 3/04 446/371 |
| 2007/0212456 A1 | * | 9/2007 | Axelrod | A23K 50/40 426/132 |

(Continued)

*Primary Examiner* — Yvonne R Abbott-Lewis
(74) *Attorney, Agent, or Firm* — Stephen E. Zweig

(57) ABSTRACT

A therapeutic toy device for an animal user. The device comprises an internal spine simulator comprising a plurality of weighted vertebra simulators, all coupled together in a manner intended to somewhat resemble the spine of a prey animal. The toy device is configured so that when the animal user plays with the toy, the act mimics the sensation of tackling an actual prey animal. This satisfies the animal's predator instincts, and thus gives the animal a more meaningful and satisfying sensory motor experience, thus improving well-being. The device will be surrounded by a covering, and optionally configured with other elements such as one or more straps, limb simulators, internal stuffing, and other features. The toy device may be configured in varying weights and configurations based on the size, weight and play-drive of an animal user.

19 Claims, 7 Drawing Sheets

(56) References Cited

U.S. PATENT DOCUMENTS

| | | | |
|---|---|---|---|
| 2008/0146116 A1* | 6/2008 | Di Lullo | A01K 15/025 446/297 |
| 2011/0297104 A1* | 12/2011 | Axelrod | A01K 15/026 119/709 |
| 2014/0230752 A1* | 8/2014 | Yerton | A01K 15/026 119/709 |
| 2016/0113243 A1* | 4/2016 | Mullin | A01K 15/026 119/709 |

* cited by examiner

THERAPEUTIC TOY DEVICE FOR AN ANIMAL

CROSS REFERENCE TO RELATED APPLICATIONS

This application is a continuation in part of application Ser. No. 15/390,482, filed Dec. 24, 2016, now U.S. Pat. No. 10,299,464, issued May 28, 2019; application Ser. No. 15/390,482 claimed the priority benefit of U.S. provisional application 62/298,648, THERAPEUTIC TOY DEVICE FOR AN ANIMAL, inventor Mary Beth Evans, filed Feb. 23, 2016; the entire contents of these applications are incorporated herein by reference.

BACKGROUND OF THE INVENTION

Field of the Invention

This invention is in the field of toys intended for use by animals; in particular, toys intended to produce a therapeutic calming effect.

Description of the Related Art

Various toys for animals are known in the art. These include the adjustable weight toy ball concepts of Harrington (US patent publication 2014/0299070), the therapeutic chew device of Owens (U.S. Pat. No. 6,050,224), the tug toys of O'Rourke (U.S. Pat. No. 5,092,272) and other devices. Other work in the field includes Axelrod U.S. Pat. Nos. 8,789,496 and 9,078,415; Yerton U.S. Pat. No. 9,357,750; and Handelsman U.S. Pat. No. 6,112,703.

BRIEF SUMMARY OF THE INVENTION

Like humans, animals have a sensory-motor system in need of stimulation. If this need is not met dysfunction may occur and animals become upset, anxious, and in need of calming. The invention is based in part, on the insight that some of the same neurobiological concepts used for humans may also provide useful insight into new types of therapeutic toys for animals intended to organize their nervous system and calm the animal.

The invention is also based, in part, on the insight that animal organisms, including pet dogs and cats, but also including various types of zoo predator animals such as bears, wolves, other cat species, and other zoo animals, have a primal need to participate in an authentic sensory-motor experience of manipulating/tackling prey. This pleasurable occupation of hunting/tackling prey, which includes biting, shaking, mouthing, carrying, pulling, and perhaps even chasing and stalking satisfies the animal's sensory-motor needs. It should be apparent, however, that such sensory motor needs cannot be easily fulfilled in most artificial environments such as human homes and zoos. In other words, the animal's primal sensory needs with regard to manipulating/tackling/playing with prey are not met. The stability of animal organisms' mental state is dependent on adequate sensory and perceptual contact with the world. Studies have shown the following common features in cases of poor sensory stimulating environments resulting in intense desire for additional sensory stimuli or adapting to stagnant environment resulting in aberrant behavior such as: aggression, barking, chewing, digging, excitable, escaping, fur pulling, pacing, jumping, or apathy, depression, anxiety, uninterested, withdrawn, and poor appetite.

The invention is also based, in part, on the insight that a toy device for such animals, which can be made from either natural or synthetic materials, should otherwise activate at least some of the animal's instinctive predatory chase drive. Here natural materials, such as a wool covering, may have the advantage of better reproducing the "mouth feel" of prey, while synthetic materials may provide higher durability, lack of allergens, and reduced odors.

Here, an underlying objective is to produce a toy device, made from either synthetic components or natural components, which nonetheless mimic many of the sensory-motor experiences that an animal, such as a mammal, will experience while manipulating a prey animal. Typically, this toy device will encase a weighted vertebrate-like internal structure. The toy device animal will have a weighted backbone and may either have an outward appearance similar to real prey animals, or alternatively take on other configurations. Such a toy device will often comprise a covering formed from either a synthetic or natural material, and also some sort of internal structure, often produced by an internal structure designed to mimic the prey animal's backbone. When the user animal (i.e. the pet or zoo animal) manipulates/plays with this toy device, the pet or zoo animal will encounter an opposing force against gravity, and/or tactile chewing sensations, produced by the toy device's internal weighted backbone and/or limbs. With pet or zoo animal manipulating/playing this type of weighted toy, a sensory-motor message is sent through the animal's central nervous system, enhancing the brain's perception of internal and external cues. The brain organizes the sensations to give meaning to what is experienced, thus integrating sensory information, and allowing the animal to respond in a more purposeful and calm manner.

BRIEF DESCRIPTION OF THE DRAWINGS

FIG. 2 shows an alternative embodiment of the device previously shown in FIG. 1A, further comprising a force transducing mechanism and a weighted material configured to adjust the weight of the device to between 1-35% of the weight of an animal that the device is configured for.

DETAILED DESCRIPTION OF THE INVENTION

Figure 1A:
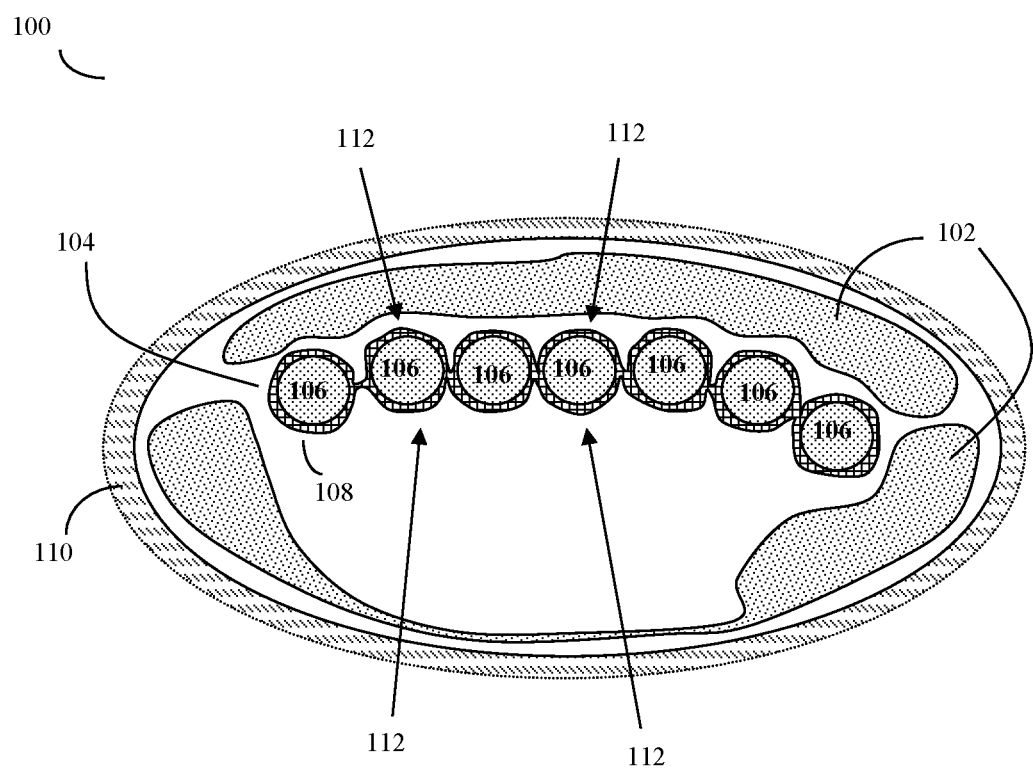
FIG. 1A shows an embodiment of the device comprising the internal spine simulator and a stuffing (e.g. wrapping, fill) material both surrounded and enveloped by a chew resistant covering.

Regarding terminology: In standard use, a "vertebra" is the singular form of a spinal column bone, while vertebrae is the plural form. In the context of this disclosure, an internal spine simulator composed of a plurality of individual vertebra simulators is taught. However, given the context that a plurality of individual vertebra simulators is taught, a plurality of vertebrae simulators are also being taught. In general, unless otherwise specified, the two terms will be used somewhat interconvertible manner. That is, for the purposes of this discussion, an internal spine simulator comprising a plurality of individual vertebra simulators or vertebrae simulators is being taught.

The invention is based, in part, on the insight that an animal's motor response relies on sensory feedback from proprioceptors (various types of biological force and position sensors typically located in skeletal striated muscles). The proprioceptive system is an intricate and complex biological network that helps an animal (and a human) modulate its movement and balance. This system is typically sensitive to very small shifts in muscle alignment or equilibrium. The system also gives the animal's central nervous system continuous reports on muscular tension or relaxation. The proprioception system also enables flexible redirection of animal's attention as well as facilitating nervous system control of the subtle movements of the animal's eyes, jaws, paws and other portions of the animal.

Thus, for example, when an animal manipulates/plays with an object and encounter an enhanced force against gravity, the proprioceptive system provides feedback to the animal's nervous system that gives meaning to what is experienced. Other information obtained from playing/manipulating objects includes vestibular sensory input (the sense of movement, centered in the inner ear). Here various types of head movement can stimulate the vestibular receptors. The tactile sense is activated through skin and membranes such as the mouth.

The present invention is also based, in part on various studies showing that enriched environments, both for animals and humans, are necessary for the animal's sensory motor needs to be met resulting in a well-balanced and happy animal organism. Here, the present invention is directed towards providing an animal toy device to enrich the occupation of play by providing a more realistic/authentic, predatory hunting sequence and sensory-motor experience. When the animal manipulates or otherwise plays with the toy device i.e. shaking, carrying, tugging, tossing, chasing. The result is often a calmer and happier pet.

Note that in this discussion, it is assumed that the user animal has a typically integrated sensory system and appropriate proprioceptor cells located in skeletal muscles and joints that can sense differences in force and the direction of force when an animal manipulates the object. As well as typical tactile and vestibular systems capable of processing of sensory information.

FIG. 1A shows an embodiment of the device comprising the internal spine simulator and the synthetic stuffing, both surrounded and enveloped by a synthetic fur covering.

In some embodiments, the invention's therapeutic toy device (100) may comprise a stuffing material (102). In this may be a synthetic stuffing (e.g. polyester fiber, polypropylene, polyester fiberfill) although natural stuffing materials such as cotton fiber, wool, and the like may also be used. The therapeutic toy device will also comprise an internal spine simulator (104). This internal spine simulator is intended, to some extent, to mimic some of the mechanical characteristics of a prey animal spine and/or spine associated elements such as ribs. This internal spine simulator will often be made from non-bone material.

In a preferred embodiment, this internal spine simulator (104) will comprise a plurality of vertebra simulators (106). A vertebra simulator is designed to at least somewhat reproduce the tactile sensation that an animal might obtain when chewing on or otherwise manipulating real vertebrae.

The internal spine simulator will often comprise at least two vertebra simulators, often three, four, five, six, seven, eight, nine, 10 or more vertebra simulators may be used. Indeed, configurations with up to thirty or more vertebra simulators are contemplated. These vertebra simulators will typically be configured in a flexible linear array, thus allowing the various vertebra simulators to move (e.g. bend or twist) with regards to each other, while still retaining an essentially linear configuration. Here the model is a natural prey animal vertebra where the harder and more rigid bone vertebra are able to bend, flex and rotate with respect to each other due to the positioning of intervening and more flexible intervertebral disks.

Although in some embodiments, the vertebra simulators (106) could actually be real vertebra bones (preferably appropriately cleaned and sized), in a preferred embodiment, the vertebra simulators will themselves be made of a non-bone material. This non-bone material can comprise a variety of semi-hard to hard materials, such as synthetic rubber, ceramic, metal, or other materials. As a general rule, the non-bone material should have a Shore A durometer value of at least 40 (which corresponds to a minimum hardness comparable to a synthetic rubber pencil eraser), and this value can be much harder (e.g. rocks or metals may also be used).

An individual vertebra simulator (106) need not have the squat and approximately cylindrical shape associated with a natural vertebra. Instead a vertebra simulator may be a substantially compact (e.g. generally convex or at least substantially non-concave) solid (e.g. a sphere, cylinder, or other shape) (107) or even a plurality of smaller solids that may be a fraction of an inch in diameter, such as approximately between 0.005 inches (sand grain sized solids) to 1 inches (pebble sized solids), all held together by an external vertebrae covering, into the approximate shape of an individual vertebra, as is shown in FIG. 1B.

Examples of suitable spheres include ball bearings and the like. Indeed, ball bearings, with an approximate diameter of about 1 inch (e.g. a diameter between ½ inch and 1½ inches, or a radius between ¼ inches and ¾ inches), particularly solid ball bearings formed from ceramics, plastics, or steel, can be particularly useful as vertebra simulators. This is because the rounded surface of the ball bearing does not present any crevices that might damage the animal's teeth. Although many different types of materials may be used for the ball bearing, use of steel type ball bearings, particularly steel ball bearings weighing approximately ½ to 2 ounces each (e.g. 1 ounce each), can be particularly useful for dogs, and similar sized animals, because this gives each vertebra simulator enough "heft" to provide additional tactile feedback to the animal.

Figure 1B:
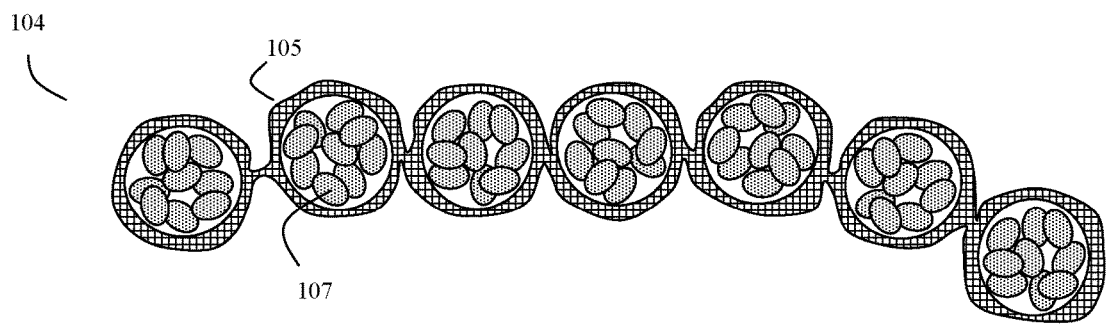
FIG. 1B shows an alternative embodiment of an internal spine simulator.

FIG. 1B shows an embodiment where each individual vertebra simulator is composed of a plurality of small and relatively hard gravel, granule, or pebble sized objects (107), here about diameters of approximately 0.1 to 0.3 inches. Here these objects will be called "granules". These granules may be held into individual vertebra simulators (106) by various means, such as by covering or encapsulating the granules with a vertebra covering material (105), which is distinct from the outer covering of the toy device (110). This vertebra covering material can be a synthetic fabric (e.g. nylon fabric) or other material, held together by stitching. Alternatively, the individual granules may be encapsulated into a flexible material such as rubber, synthetic rubber, or other type polymeric material.

When the vertebra simulators are composed of a plurality of granules, the number of granules (107) in each vertebra simulator (106) may vary according to the size of the vertebra simulator and the size of the granules. Generally, enough granules will be packed into each individual vertebra simulator to produce a relatively firm structure that will somewhat deform or crush upon receiving a bite force from the animal's teeth.

The exact amount by which the vertebra simulator may compress or crush upon receiving a bite force from the animal user's mouth may vary. The general objective is to have the vertebra simulator crush enough to satisfy the animal's natural instincts. Too much crushing may be unsatisfying to the animal, as well as too little crushing. Often intermediate crush amounts, such as crushing to 90%, 80%, 70%, 60%, 50%, 40%, 30%, 20% or even 10% of the original thickness upon receiving typical animal bite forces may be best.

Some of the larger breeds of dogs can produce a force of around 300 pounds or more per square inch. Thus a vertebra simulator composed of small granules, and optimized for a particular type of user animal, might be packed with sufficient number of the granules (e.g. number of granules per cubic inch) that the vertebra simulator might compress to about half or a quarter of its original diameter when exposed to a force of approximately 300 pounds or more per square inch. Variations of up to a factor of 10 in either direction around this approximate range are contemplated. In general, the vertebra simulators may be "tuned" with a granule type and granule density (e.g. number of granules per square inch) to produce a crushability that is proportionate to the bite force of the user animal in question.

Figure 1C:
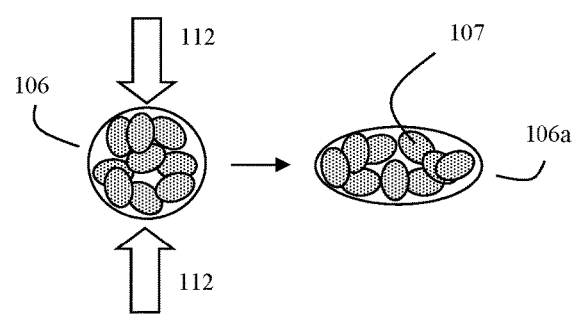
FIG. 1C shows how a vertebra simulator, composed of a plurality of individual granules, may at least temporarily deform or crush as a result of a bite force from an animal.

An example of this bite force induced vertebra simulator crushing is shown in FIG. 1C. Here bite force (112) deforms the vertebra simulator from a first shape (106) to a second and partially crushed shape (106a). After this crushing process, due to shaking by the animal and normal rearrangement of the various granules (107) inside the vertebra simulator, the crushed shape (106a) will at least partially reverse, producing the original shape (106).

Figure 1D:
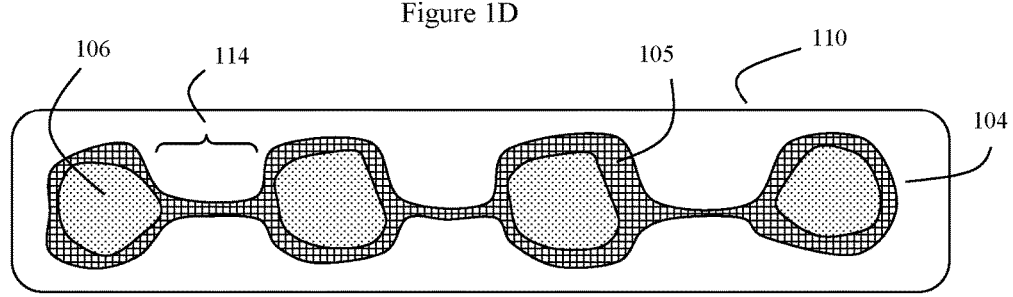
FIG. 1D shows an alternative "bumper style" embodiment of the device. Here, in addition to having an overall elongated rectangular shape, there is also a greater separation between the individual vertebra simulators in the internal spine simulator.

FIG. 1D shows an alternative "bumper style" embodiment of the device. Here, in addition to the device having an overall "bumper style" elongated rectangular shape; there is also a greater separation (114) between the individual vertebra simulators (106) in the internal spine simulator (104).

In some embodiments, each vertebra simulator will have some appreciable density, such as a density of that of water or greater (e.g. equal to or greater than 1 gram per cubic centimeter). Often each vertebra simulator will have an appreciable weight, such as 10, 15, 30 grams or more, often on the order of ⅓, ½, 1, 2, 3, 4, 5, 6, 7, 8, 9, 10, 11, 12, 13, 14, 15, 16 or more ounces (as expressed in ounce units).

In other embodiments, the density of each vertebra simulator, or at least the density of the internal spine simulator as a whole, may be configured to have a density less than that of water. Such embodiments may be useful in the event that it is desired to have the device (100) as a whole be capable of flotation in water.

Each individual vertebra simulator, regardless of shape, can be viewed as having a maximum radius. In some embodiments, where the internal spine simulator is intended to somewhat mimic the bending characteristics of an actual spine, when the plurality of vertebra simulators are configured in a flexible linear array, the maximum separation between each individual vertebra will be is less than this maximum radius. However other spacing (114) (e.g. longer separations such as 1× maximum radius, 2× maximum radius, 3×, 4×, 5×, 6× maximum radius or more) are also possible and are also contemplated by the invention. In all of these configurations, the minimum separation may be zero (e.g. the vertebra simulators can be touching), or ¼ or ½ the maximum radius.

For standard house pets (e.g. dogs, cats, and the like) the radius of each individual vertebra can vary between ⅛ inches and 2 inches. For more exotic animals such as zoo animals, the radius of each individual vertebra can vary between ⅛ inches to 4 inches (think tiger chewing on a water buffalo carcass). So different sized animals may be provided with different sized therapeutic toys, each with an appropriately sized internal spine simulator with appropriately sized individual vertebra simulators.

The various individual vertebra simulators (106) can be combined to form an internal spine simulator (104) in various ways. Generally, either the various individual vertebra simulators can be constrained in a linear array by embedding the individual vertebra simulators between a covering or covers formed from a flexible fabric or flexible sheet of material (108). This can be, for example, synthetic woven or non-woven fabric or other flexible sheet of material. This flexible sheet of material can, for example, be formed from flat nylon webbing or similar material. The dimensions of this webbing may be selected to encase each individual vertebra simulator, and may extend to the length of the total internal spine simulator or greater if desired.

A specific example here, for individual vertebra simulators with an approximate diameter of about ½-1 inch, can be flat nylon webbing about 3 inches wide, and as long as desired (e.g. depending upon the number of individual vertebra simulators used and the spacing between each one) with a strong breaking strength (ideally thousands of pounds or more) and a relatively high melting point (e.g. above 300 degrees Fahrenheit or more). Another example of a suitable non-woven fabric or flexible sheet of material (108) can be dura-fused natural or synthetic leather, such as a multiple layer configuration with one or more layers of leather and jute fused together. Here the main criterion is that the flexible sheet of material should be durable to stand up to repeated mechanical stress due to chewing, tugging and moisture (often from the animal's mouth). In general, natural or synthetic leather, rubber, plastic, cotton, jute, animal hair, woven, and non-woven materials may be used.

Although in some embodiments, no joints may be used, in other embodiments, the plurality of individual vertebra simulators (106) can be coupled together by alternative arrangements, such as by using at least one joint and/or connector between each individual vertebra simulator thus in effect forming a type of flexible chain. Here again, this later design also allows the individual vertebra simulators to move (e.g. twist or bend) relative to its neighboring individual vertebra simulators, while still forming a flexible linear array.

In an alternative embodiment, the plurality of vertebra may be formed from a molded rubber or other type of flexible synthetic polymer. Here, each vertebra may either consist of substantially thicker portions of the polymer, with thin portions of the polymer serving as flexible joints between the vertebra. Alternatively, the vertebra simulators may be embedded into the flexible synthetic polymer. Here, for example, a mold could be first filled with the individual vertebra simulators, and then the polymer (in melted or substantially unpolymerized form) introduced into the mold, and allowed to harden, thus encapsulating the individual vertebra simulators and also joining them together with joints made from the hardened or polymerized form of the polymer.

Generally, the internal spine simulator (108) and the natural or synthetic stuffing (102) will be completely enveloped in a flexible, chew resistant covering (110), such as a natural or synthetic fur covering. In addition to synthetic fur, natural materials such as woven or nonwoven wool and the like may also be used. The net effect of the covering (110) is to thereby form a body configured so that when the animal chews or bites the therapeutic toy device (here force from the teeth on the animal's jaws is represented by the arrows (112), the stuffing (102) and fur covering (110) deform, thus allowing the animal to detect resistance force produced when the animal's teeth, separated by the synthetic fur covering and the stuffing from the vertebra simulators, encounter resistance produced by the vertebra simulators on the internal spine simulator (108). More specifically, the animal's various proprioceptors detect this resistance.

In some embodiments, the device will be configured with an approximate size and weight to represent the animal's typical or average wild prey. Thus, depending on the size of the animal, the device might be configured with the approximate size and weight of various types of wild animals such as birds, rats, squirrels, rabbits and the like. Indeed, a range of devices may be produced and sold, where each device is broadly between about 1 to 100% or more of the intended animal user weight, often between about 1 to 35% of the weight of the animal user, or even more specifically between about 1% to about 10% of the weight of the animal user. Thus, for example, for a toy device intended for use by a 30-pound dog, the toy might weight about 0.3 to 3 pounds.

Embodiments optimized for dogs and similar type animals:

Some embodiments of the device may be optimized for dog owners. These can be owners with apprehensive or anxious dogs (that need calming) or housebound dogs that need some exercise and stimulation. Certain embodiments of the device may also be useful for dog trainers as well.

Figure 1E:
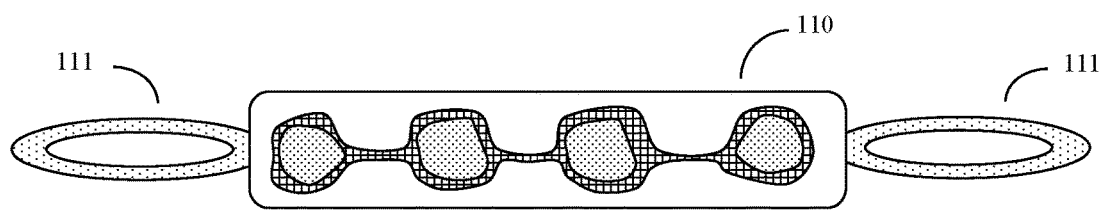
FIG. 1E shows the "bumper style" embodiment of the device, which can also include one or more carrying straps.

FIG. 1E shows a "bumper style" embodiment of the device, which in some embodiments may also comprises at least one carrying strap (111), which may be at least one loop of material, attached to the device (110) at one end, configured to allow the device to be carried or hung up on a hook when not in use. The strapping can also be useful for creating toss and "tug" handles so that the owner can engage in games of "fetch", or "tug of war", with the animal as desired. In some embodiments, this carrier strap (111) may be attached to both ends of the device (110). In other embodiments, this carrier strap (111) may only be attached to one end of the device (110).

These one or more straps (111) may comprise leather, fabric, rope, or other natural or synthetic material. The strap(s) may attach to the device (110) by sewing, by passing through a grommet that itself is affixed to the device (110), gluing, riveting, or other method. Usually, each strap will be placed near the extreme long ends of the device. Typically, some embodiments may have no strap (111), some embodiments, may have one strap (111), and some embodiments may have two straps (111). Typically, each strap (111) placed at opposite ends of the device (110) (e.g. at extreme opposite ends of the long side of the device).

In some embodiments, the bumper style configuration of the device, shown in FIGS. 1D and 1E, will have a total length (including any optional strapping 111) of between about 12 inches and 24 inches. The total weight of the bumper style configuration may be between about half a pound and two pounds, and the width will between about 3 to 5 inches.

The bumper style configuration can have a total width greater than one inch, and can even be up to 2-3 inches thick. The bumper style device will often comprise about 5-12 vertebra simulators. In a preferred embodiment, the vertebra simulators will have a diameter between about ¾ inches and 1⅛ inches, and be separated from each other by a space of approximately 1 inch (e.g. ½ inch to 1½ inch). For a 1-inch diameter (½-inch radius) sphere, this is about 1× to 3× the radius of the sphere.

As previously discussed, in some embodiments, the vertebra simulators may be housed or sewn inside of an inner support, such as a woven polypropylene or other material type inner support. For better durability, it may be desirable to individually stitch each individual vertebra simulator inside this inner support. This inner support, containing the various vertebra simulators may then be sewn or otherwise attached inside the outer covering. The optional strapping, such as a leather or synthetic material strap, may then be sewn, riveted, or otherwise attached to the outer covering.

Although, as previously discussed, a wide variety of synthetic and natural materials may be used for this outer covering, to create a more natural "mouth feel" to the animal, a wool or other natural animal fur material may be desirable. In particular, the wool texture and chemistry can better simulate the feel and taste of a prey animal.

This particular bumper configuration, although still useful for a variety of different animals, is particularly useful for dogs, and is also optimized for cost-effective manufacturing as well. The combination of the wool covering and texture appeals to dogs, while the weight (½ pounds to 2 pounds) simulates a typical weight of a small prey animal. The straps can help encourage the dog to engage in tugging and shaking activity, which are normal and indeed encouraged behaviors for this type of animal. In this embodiment, the dog may be encouraged to engage with the device as a chase and return type play item, in addition to being a potential chew toy as well.

The net effect is to create a toy that can have both a therapeutic and calming aspect, while on the other hand also be used for more strenuous and authentic play activities.

Other Embodiments

Figure 2:
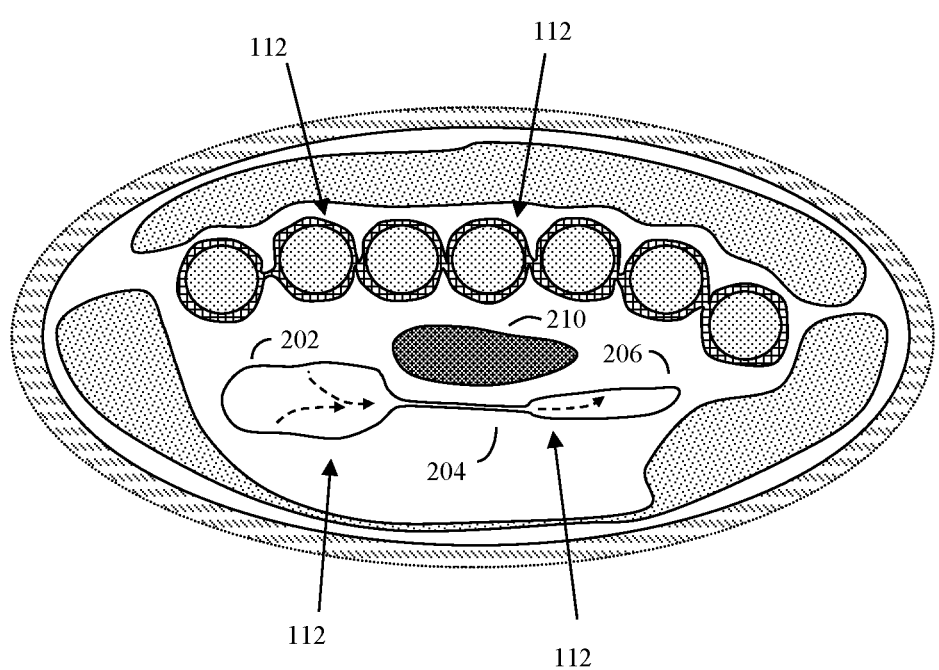

In some embodiments, to make the experience of manipulating/tackling a prey animal still more realistic, the device may further comprise a force transducing mechanism. FIG. 2 shows an alternative embodiment of the device previously shown in FIG. 1, further comprising a force transducing mechanism (202-204) and a weighted material (210) configured to adjust the weight of the device to between 1-35% of the weight of the user animal that the device is configured for.

This weighted material (210) may comprise either a solid material such as a wood, bone, metal, rubber, plastic or ceramic, particulate material such as rocks, sand, gravel, metal shavings and the like, typically with a density greater than water, contained in a flexible enclosure, and the like.

In some embodiments, this force transducing mechanism may be a pneumatic device composed of various hollow and elastic chambers (202), (206), possibly connected by a thin tube (204). Here application of force by the animal's jaws (112) on chamber (202) might cause air or fluid to flow over thin tube (204) to an elastic hollow chamber (206), thus creating a transfer of force that can be detected by the animals. Alternative force transducing mechanisms involving various types of spring and lever arrangements can also be done. Regardless of configuration, the concept is that application of mechanical force by the user animal's jaws of results in force or movement being transferred and reappearing at one or more different regions of the device.

Often real prey animals will have limbs (e.g. heads, wings, legs, and the like). In some embodiments, the device may also comprise a plurality of limb simulators. Head simulators (discussed shortly) may also be provided. These head and limb simulators can be provided in either realistic (e.g. one head and four limbs) or non-realistic configurations (e.g. two heads, six limbs, and so on). These simulators, and the body of the device itself, may be created in arbitrary shapes, including animal shapes, geometric shapes (e.g. rectangular shapes), and other shapes.

Figure 3:
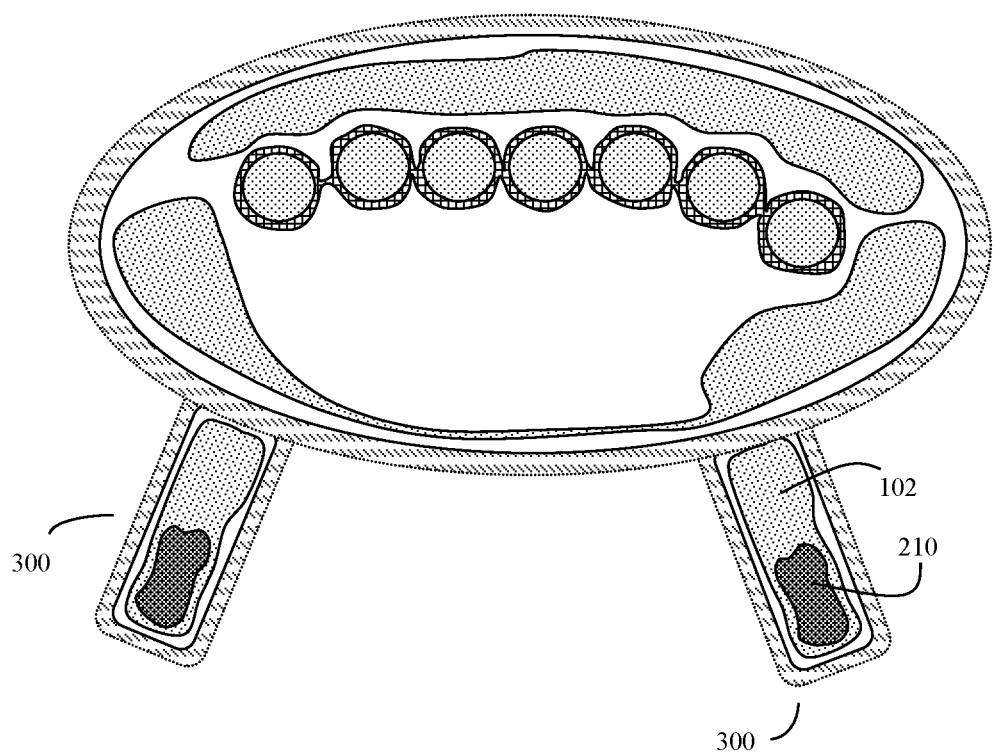
FIG. 3 shows an alternative embodiment of the device previously shown in FIG. 1A, further comprising a plurality of limb simulators each comprising a fill material (e.g. stuffing) and a weighted material.

FIG. 3 shows an alternative embodiment of the device previously shown in FIG. 1A, further comprising a plurality of these limb simulators (300). In this example, each limb simulator (300) further comprises stuffing and a weighted material.

In these embodiments, the device can further comprise a plurality of limb simulators (300). These limb simulators (300) can, for example, comprise stuffing (such as the previously discussed stuffing 102) and optionally also a weighted material (such as the previously discussed weighted material 210). This stuffing (102) and optional weighted material (210) can be completely enveloped in a flexible, chew resistant, synthetic covering (often the same synthetic fur covering 110) used for the main portion of the device).

Here, chew resistant means that the material can withstand repeated chewing or biting by the animal, and does not fall apart upon the initial chewing or biting event.

These limb simulators will be firmly attached to the main body by a secure means (e.g. fusing, sewing, riveting, molding and the like) so that the limb simulators (300) will not be detached from the body (100) during normal chewing and even rough treatment by the animal user. In some embodiments, the plurality of limb simulators (300) are attached to the body (100) by a flexible joint configured so that when the animal user picks up the device, at least some of the limb simulators (300) are free to dangle while still being firmly attached to the body (100).

Real prey animals often have heads as well. Thus, for greater realism, in some embodiments, the device will also comprise a head simulator (shown in FIG. 4 as 400). This head simulator will generally have a fraction of the volume of the main body simulator (100), and often may have about 5% to 50% of the volume of the main body simulator. This head simulator will generally comprise at least a stuffing material (e.g. a material such as 102), generally completely enveloped in a flexible chew resistant, synthetic covering such as synthetic fur covering 110. This head simulator (400) will generally be affixed to the body (100) at a position that is near or proximate to one end of the internal spine simulator (112). This head simulator may optionally have additional details intended to create an additional resemblance to a prey animal, such as eye markings or details, ear markings or details, mouth markings or details, and the like (not shown).

To further make the device more like a "real" prey animal, in those embodiments where a head simulator (400) is present, it may also be useful to further put at least one orientation weight (410) into the main body of the device (100). This at least one orientation weight (410) will preferably be disposed in at least one region inside the body (100) with the location/region and mass of the weight (410) selected so that when the device is dropped, the orientation weight (410) will tend to force the head simulator (400) into an upright position (e.g. the device lands "head's up").

Figure 4:
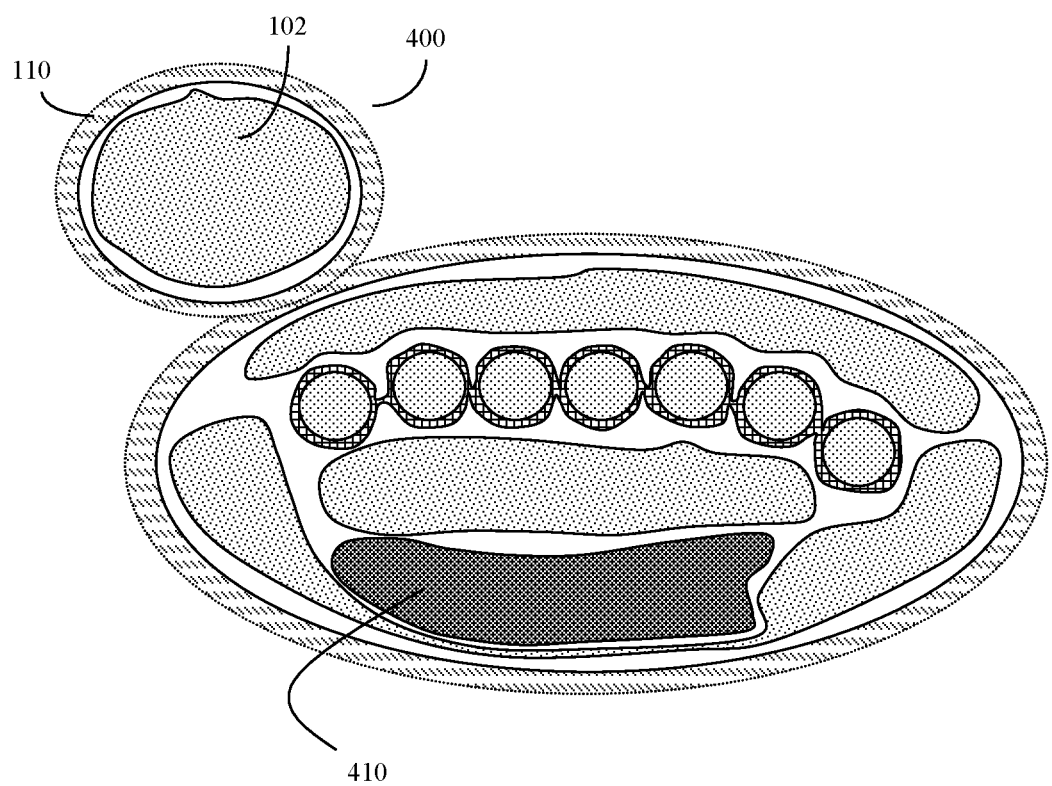
FIG. 4 shows an alternative embodiment of the device further comprising a head simulator and an orientation weight with a position and mass selected so that when the device is dropped, the orientation weight tends to force the head simulator into an upright position.

FIG. 4 shows an alternative embodiment of the device further comprising a head simulator (400) and an orientation weight (410) with a position and mass selected so that when the device is dropped, the orientation weight (410) tends to force the head simulator (400) into an upright position.

Figure 5:
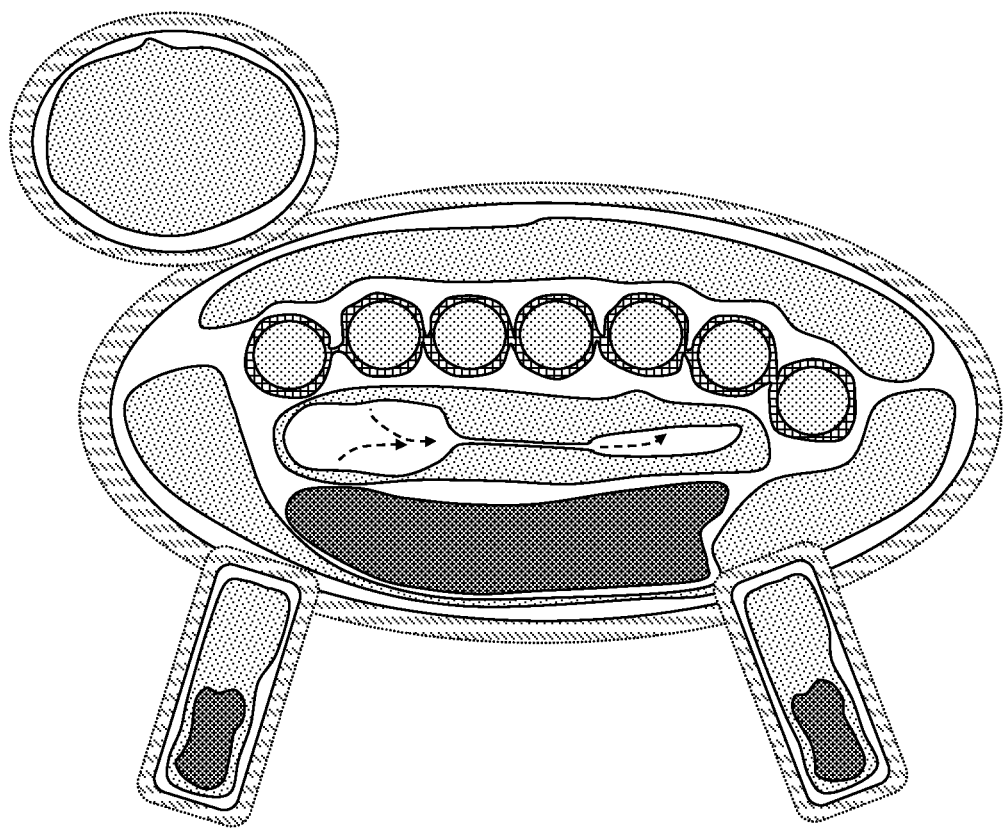
FIG. 5 shows an embodiment of the invention that comprises all of the above features, including optional force transducing mechanisms, limb simulators, a head simulator, and an orientation weight. The actual shape of the final device may, but need not, resemble a prey animal. Other shapes, such as "bumper style" rectangular shapes, as well as irregular shapes, circular shapes, and the like may also be used (bumper style is a term of art in the pet supplies industry for rectangular pet toys).

FIG. 5 shows an embodiment of the invention that comprises all of the above features, including force transducing mechanisms, limb simulators, a head simulator, and an orientation weight.

The device will typically be used at home, zoos, shelters, boarding facilities, training facilities, wildlife reserves. Generally, in an at-home environment, the device will generally be configured for situations where the user animal is a dog or a cat. However as previously discussed, in zoos or other non-home situations, the device may be configured for a greater variety of different animals. Thus, a device intended for a bear in a zoo might be considerably larger and heavier than a device configured for a small dog (such as a Chihuahua). Indeed, for some zoo animals, the 1-35% weight range might be expanded, and larger devices might be constructed in the 1%-100+% weight (of the intended animal user) range.

Distribution of sizes of body, head, and limbs, as well as weighted material (210), (410): In some embodiments, the device will be configured to have an approximate anatomical weight distribution through head, trunk (body) and limbs based on type of prey animal being simulated or not with configuration of a geometric shaping?

Use of natural materials: although synthetic materials are frequently used herein as examples of the preferred materials for this device, the use of natural materials is not disclaimed. Such natural materials can include natural fibers, wood, leather, bone, and the like, and such natural materials may also be used for some embodiments of the invention.

The invention claimed is:

1. Therapeutic toy device for an animal, said device comprising:
    an internal spine simulator, said internal spine simulator comprising a plurality of vertebra simulators configured in a flexible linear array;
    wherein each vertebra simulator comprises a single solid material with a weight between ½ ounces and 2 ounces, said material having a shore "A" durometer value of at least 40;
    wherein each vertebra simulator has a maximum diameter between ½ inches and 1½ inches, and wherein when said plurality of vertebra simulators are configured in a flexible linear array;

wherein a maximum separation between each individual vertebra is less than twice said maximum diameter;

wherein said plurality of vertebra simulators are each embedded in a flexible woven or non-woven fabric or polymer or sheet of material so as to form said flexible linear array;

said internal spine simulator completely enveloped in a flexible, chew resistant, covering, thereby forming a body configured so that when said animal bites said therapeutic toy device, said covering deforms allowing said animal to detect resistance force produced when said animal's teeth, separated by said covering, encounter resistance produced by said vertebra simulators.

2. The device of claim 1, wherein said vertebra simulator comprises a sphere.

3. The device of claim 2, wherein said sphere is a ball bearing.

4. The device of claim 1, wherein said therapeutic toy device is further equipped with an additional weighed material configured to adjust a total weight of said therapeutic toy device to between 1 to 35% of a weight of said animal.

5. The device of claim 1, wherein said device further comprises a plurality of limb simulators, said limb simulators comprising stuffing and a weighted material completely enveloped in said flexible, chew resistant, synthetic fur covering; and
wherein said each of said plurality of limb simulators are attached to said body by a flexible attachment, configured so that when said animal picks up said device, said limb simulators are free to dangle while still being attached to said body.

6. The device of claim 1, wherein said device further comprises a head simulator comprising stuffing completely enveloped in said flexible, chew resistant, synthetic fur covering, said head simulator affixed to said body at a position that is proximate one end of said internal spine simulator.

7. The device of claim 6, further comprising at least one orientation weight disposed in at least one region inside said body, said at least one orientation weight region and mass selected so that when said device is dropped, said orientation weight tends to force said head simulator into an upright position.

8. The device of claim 1, wherein said covering comprises any of a synthetic fur covering and a covering comprising natural animal hair.

9. The device of claim 1, wherein said covering comprises wool.

10. The device of claim 1 further comprising at least one strap.

11. The device of claim 1, further comprising a natural or synthetic stuffing;
wherein said internal spine simulator and said stuffing are completely enveloped in a flexible, chew resistant covering, thereby forming a body configured so that when said animal bites said therapeutic toy device, said stuffing and covering deform allowing said animal to detect resistance force produced when said animal's teeth, separated by said covering and said stuffing, encounter resistance produced by said vertebra simulators.

12. Therapeutic toy device for an animal, said device comprising:
stuffing;
an internal spine simulator, said internal spine simulator comprising a plurality of vertebra simulators configured in a flexible linear array;
wherein each vertebra simulator is at least one substantially compact solid formed from a material with a shore A durometer value of at least 40, a density of at least 1 gram/cm$^3$, and a weight of at least 1 ounce;
at least some of said vertebra simulators configured to deform or crush to 90% or less of their original thickness upon receiving a bite force from said animal;
wherein each vertebra simulator has a maximum radius, and wherein when said plurality of vertebra simulators are configured in a flexible linear array, the maximum separation between each individual vertebra is less than three times said maximum radius;
said internal spine simulator and said stuffing completely enveloped in a flexible, chew resistant, covering, thereby forming a body configured so that when said animal bites said therapeutic toy device, said stuffing and covering deform allowing said animal to detect resistance force produced when said animal's teeth, separated by said covering and said stuffing, encounter resistance produced by said vertebra simulators.

13. The device of claim 12, wherein said covering comprises any of a synthetic fur covering or a covering comprising natural animal hair.

14. The device of claim 12, wherein said plurality of vertebra simulators are each embedded in a flexible synthetic woven or non-woven fabric or sheet of material so as to form said flexible linear array.

15. The device of claim 12, wherein said therapeutic toy device is further equipped with additional weighed material so that a total weight of said therapeutic toy device is between 1 to 15% of the weight of said animal.

16. The device of claim 12, further comprising a force transducing mechanism, wherein application of mechanical force by the jaws of said animal results in force or movement being applied at a different region of said device.

17. The device of claim 12, wherein each vertebra simulator comprises a plurality of solid granules, and wherein:
said plurality of solid granules are formed into a vertebra simulator by a vertebra covering material; or
wherein said plurality of solid granules are formed into a vertebra simulator by encapsulation into a flexible polymeric material.

18. The device of claim 12, wherein said covering comprises wool.

19. The device of claim 12, further comprising at least one strap.

* * * * *